United States Patent [19]

Posey

[11] Patent Number: 4,685,454
[45] Date of Patent: Aug. 11, 1987

[54] SLEEVED JACKET RESTRAINING DEVICE

[75] Inventor: John T. Posey, Altadena, Calif.

[73] Assignee: J. T. Posey Company, Arcadia, Calif.

[21] Appl. No.: 908,862

[22] Filed: Sep. 11, 1986

Related U.S. Application Data

[63] Continuation of Ser. No. 837,551, Feb. 27, 1986, abandoned, which is a continuation of Ser. No. 743,863, Jun. 10, 1985, abandoned, which is a continuation of Ser. No. 533,053, Sep. 16, 1983, abandoned.

[51] Int. Cl.⁴ ............................................. A61F 13/00
[52] U.S. Cl. .................................................... 128/134
[58] Field of Search ......................... 128/133, 134, 128

[56] References Cited

U.S. PATENT DOCUMENTS

| | | | |
|---|---|---|---|
| 1,808,496 | 6/1931 | Dillon | 128/134 |
| 2,062,586 | 12/1936 | Lawrence | 128/134 |
| 2,478,239 | 8/1949 | Chinn | 128/134 |
| 2,782,783 | 2/1957 | Gay | 128/134 |
| 2,827,048 | 3/1958 | Lupien | 128/134 |
| 2,940,443 | 6/1960 | Baker | 128/134 |
| 3,082,764 | 3/1963 | Galanis | 128/133 |
| 3,817,245 | 6/1974 | Kroeger | 128/134 |
| 4,117,840 | 10/1978 | Rasure | 128/134 |
| 4,119,095 | 10/1978 | Lewis | 128/134 |
| 4,360,014 | 11/1982 | Manahan | 128/134 |

FOREIGN PATENT DOCUMENTS 284893 9/1965 Australia .

Primary Examiner—John D. Yasko
Attorney, Agent, or Firm—Christie, Parker & Hale

[57] ABSTRACT

A patient is restrained in a wheelchair or hospital bed by a jacket disposed around the upper torso of the patient so that it makes a snug fit around the shoulders and upper torso of the patient. The jacket includes sleeves for extending along the arms of the patient. Adjustable ties on both sides of the midriff region of the jacket ard tied to adjust the size of the jacket midriff region to fit the size of the patient and for retaining the adjusted size of the jacket. Fasteners in the form of restraining straps extend away from opposite sides of the jacket for attachment to a fixture such as the understructure of the hospital bed or wheelchair. In one embodiment, a zipper fastener opens and closes the rear of the jacket, and the zipper is offset from the rear center of the jacket so that it does not apply pressure to the spinal column of the patient when the jacket is worn. The rear of the jacket also can include restraining means for securing the upper rear portion of the jacket to the hospital bed or wheelchair. The sleeved jacket prevents the patient from raising up or sliding down in the bed or wheelchair to prevent the patient from choking himself, and it prevents the patient from pulling the jacket over his head to free himself.

8 Claims, 4 Drawing Figures

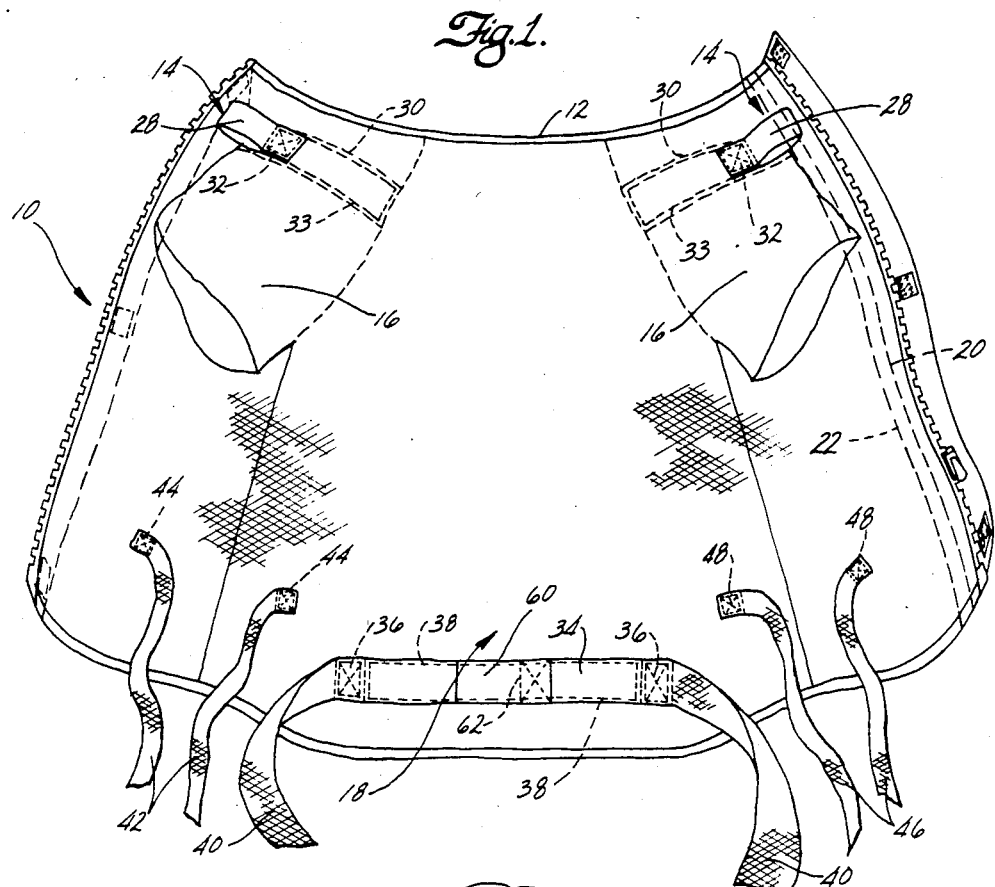
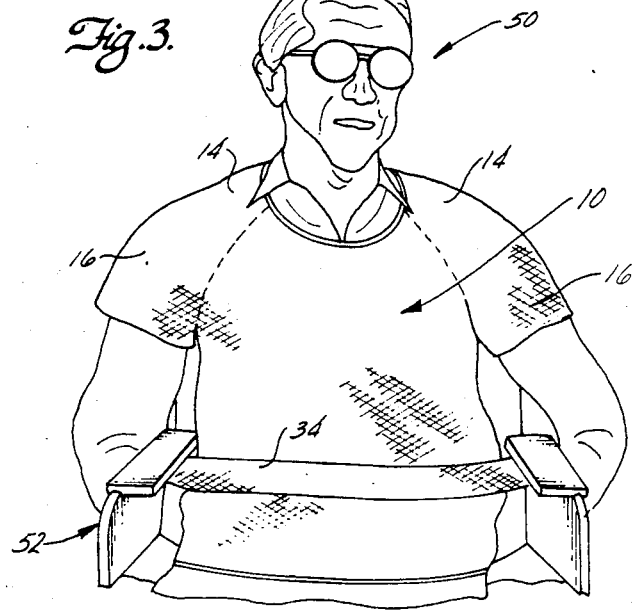

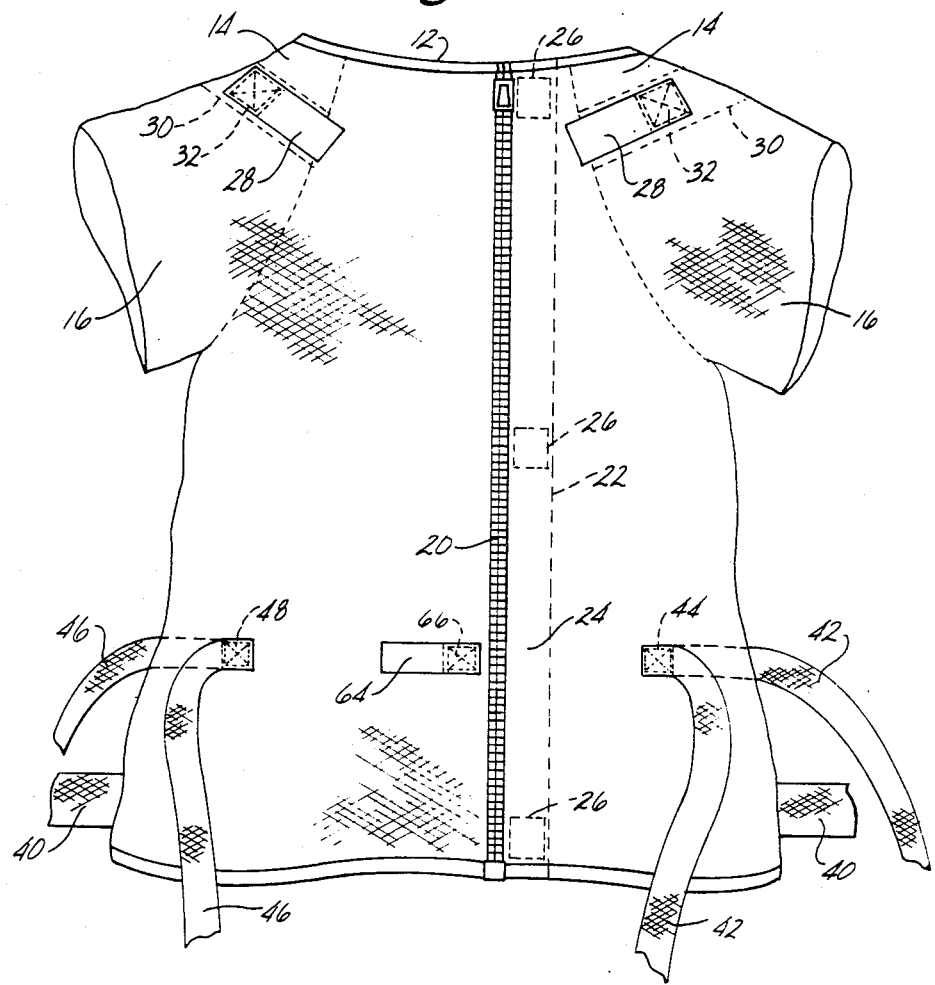
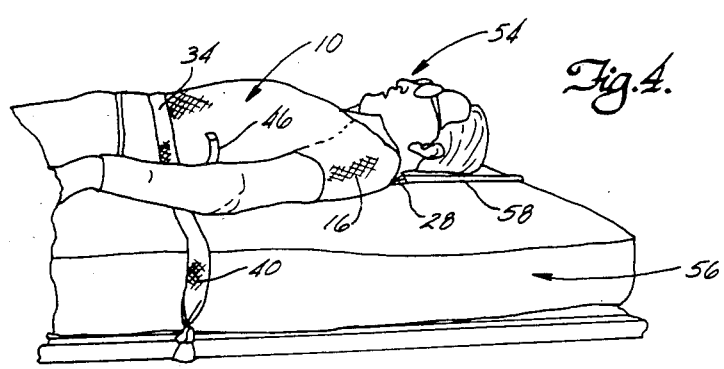

SLEEVE JACKET RESTRAINING DEVICE

CROSS-REFERENCE TO RELATED APPLICATIONS

This is a continuation of application Ser. No. 837,551 filed Feb. 27, 1986, now abandoned, which is a continuation of application Ser. No. 743,863 filed June 10, 1985, now abandoned, which is a continuation of application Ser. No. 533,053 filed Sept. 16, 1983, now abandoned.

BACKGROUND OF THE INVENTION

1. Field of the Invention

This invention relates to devices for restraining hospital patients in hospital beds or wheelchairs, for example.

2. Description of the Prior Art

Belts and shoulder straps are commonly used to secure hospital patients to beds or wheelchairs. These devices are relatively satisfactory for keeping the patient restrained, but they are not particularly comfortable because they must be tightly fastened to prevent the patient from freeing himself. Moreover, many previously known restraining devices are bulky and heavy and are therefore uncomfortable for the patient. Comfort is an important consideration because an uncomfortable patient is understandably very often uncooperative. In cases where the patient is required to rest, an uncomfortable restraining device is obviously undesirable. In order to improve patient comfort, restraining devices in the shape of a vest have been worn on the patient's upper torso. Straps on the vest are then fastened to the bed or wheelchair. Vests, however, can be uncomfortable if a zipper or other fastener at the rear of the vest constantly applies pressure against the patient's spinal column during use. A vest type restraining device also may not provide the required security for a patient. The patient may raise up and possibly choke himself on a vest, or the patient may slide down and either choke himself or pull the vest over his head to free himself.

This invention provides a restraining device that is comfortable for wheelchair and hospital patients while also providing added security since the patient cannot raise up or slide down, or otherwise pull the restraining device over his head.

SUMMARY OF THE INVENTION

Briefly, this invention provides a restraining device in the form of a sleeved jacket worn on the patient's upper torso. The sleeved jacket has ties on each side for use in adjusting the sleeved jacket to make a comfortable yet snug fit on the patient's upper torso. Restraining straps on a midriff portion of the jacket extend away from the sides of the jacket for attachment to remote portions of a bed or wheelchair. The jacket avoids the discomfort associated with shoulder straps and the like because it allows the patient to move his arms and shoulders rather freely without producing undue pressure around his shoulders. The straps are not wrapped around the patient's midriff and thereby provide a substantial degree of lateral movement for the patient's lower torso. However, the jacket provides added security because the sleeves in the jacket, combined with the jacket's close fit to the patient's upper torso and the restrained lower portion of the jacket, prevent the patient from raising up, sliding down, or pulling the jacket over his head.

In one embodiment, added comfort is provided by a zipper or other fastening means on the rear of the jacket being offset from the center of the jacket so that the zipper or fastening means do not cause added pressure on the patient's spinal column. In another embodiment, fastening means such as shoulder loops on the rear upper portion of the jacket provide added restraint against removal of the jacket by the patient.

These and other aspects of the invention will be more fully understood by referring to the following detailed description and the accompanying drawings.

DRAWINGS

FIG. 1 is a perspective view showing the front side of a sleeved jacket restraining device, in which the rear of the jacket is open.

FIG. 2 is an elevation view showing the rear side of the restraining jacket, in which the jacket is closed.

FIG. 3 is a perspective view showing the sleeved jacket restraining device in use on a wheelchair patient.

FIG. 4 is a perspective view showing the sleeved jacket restraining device in use on a hospital bed patient.

DETAILED DESCRIPTION

Referring to FIGS. 1 and 2, a restraining device according to principles of this invention includes a sleeved jacket 10 having a top edge 12 for extending around the patient's neck when the jacket is worn, a pair of shoulder regions 14 extending over the patient's shoulders, and a pair of sleeves 16 at the sides of the jacket for encircling the patient's arms. The sleeves extend for about one-half the length of the patient's upper arms (to about the midpoint of the distance from the shoulders to the elbows). The jacket extends downwardly a sufficient distance to define near its bottom a midriff section 18 adapted to be disposed around the midriff of the patient when the jacket is worn. The jacket opens and closes in the rear, and a zipper 20 is fastened to close the jacket around the patient's upper torso. A narrow vertical margin 22 at the rear of the jacket extends outboard of one portion of the zipper. A vertical margin 24 at the rear of the jacket inboard of the other portion of the zipper overlaps the narrow margin 22. Cooperating Velcro fasteners 26 are vertically spaced apart along the overlapping marginal portions 22 and 24. The fasteners are attached to one another in the well known manner for closing the rear portion of the jacket. The zipper can be fastened, if desired, to secure the jacket in its closed position. As illustrated best in FIG. 2, the length of the zipper is offset from the rear center of the jacket so that the zipper, when closed, is not aligned with the patient's spinal column.

Left and right restraints in the form of loops 28 are fastened to the rear left and right shoulder regions of the jacket. Preferably, a separate elongated reinforcing strap 30 is fastened to the inside of the rear left and right shoulder regions of the jacket. Each loop 28 is fastened to a corresponding reinforcing strap by stitching 32. The reinforcing straps are fastened by stitching 33.

A long flexible strap 34 is secured to the front midriff section 18 of the jacket. Stitching 36 and 38 fastens the strap across the front of the jacket, leaving long left and right flexible restraining straps 40 extending freely away from the left and right sides of the jacket.

A pair of horizontally spaced apart right side ties 42 are secured to the right side of the jacket by stitching 44. The ties are flexible straps that extend freely away from the right lower side portion of the jacket. A similar pair of horizontally spaced apart left side ties 46 are secured by stitching 48 to corresponding portions of the left lower side of the jacket.

As shown in FIG. 1, a loop 60 can be affixed to the middle of the lower front of the jacket by stitching 62. A cooperating loop 64 can be affixed to the middle of the lower back of the jacket by stitching 66, as shown in FIG. 2.

In use, the sleeved jacket 10 secures a patient to a bed, wheelchair, or the like. FIG. 3 illustrates use of the jacket for restraining a patient 50 sitting in a wheelchair 52. FIG. 4 illustrates use of the jacket for restraining a patient 54 lying in a hospital bed 56. The jacket is placed on the upper torso of the patient by extending the patient's arms through the sleeves and then pulling the jacket behind the patient. The fasteners 26 can be fastened before the zipper 20 is used to close the rear of the jacket. The right side ties 42 are then pulled toward one another and tied, and the left side ties 46 are also pulled toward one another and tied. The side ties provide adjustment for each side of the jacket so that the jacket is comfortable, yet fits closely to the size and shape of the patient's upper torso. The side ties are preferably tied so that they cannot be loosened or untied by the patient. The shoulder sections of the jacket fit snuggly and comfortably around the patient's shoulders, and the sleeves extend around the upper portions of the patient's arms. The jacket extends downwardly so that its midriff section is disposed snuggly yet comfortably around the midriff of the patient. Right and left portions of the restraining strap 40 are then extended away from the sides of the patient for attachment to the understructure of the wheelchair or the bed at locations remote from the patient so that he is unable to free himself. The restraining loops 28 also can be used to provide additional restraint. For a wheelchair patient, the loops may be attached to the rear handles of the wheelchair, or a strap (not shown) may be threaded through the loops and attached to the handles of the wheelchair. For a patient in a hospital bed, a strap 58 can be threaded through the loops 28 and attached to remote locations of the bed's understructure. When the jacket is in place, the zipper fastener 20 is offset from the patient's spinal column so that added pressure against the spinal column is not produced by the zipper as the patient either sits in the wheelchair or lies in the hospital bed. A crotch strap (not shown) can be placed between the patient's legs and connecting the two loops 60 and 64 shown in FIGS. 1 and 2. This can add further safety in preventing the patient from sliding down in the jacket.

The sleeved jacket effectively restrains the patient in the wheelchair or bed. The sleeves of the jacket combined with the ties at the sides and the waist straps at the bottom restrain the patient from raising up, sliding down out of the jacket, or pulling the jacket over his head. Although the patient is effectively restrained by the jacket, he remains comfortable. The jacket provides substantial freedom of movement for the patient's upper torso, his arms and shoulders. This movement is possible without producing the annoying pressure on the upper torso and shoulders normally associated with tight shoulder straps, or the like. Since the waist straps are not wrapped around the midriff of the patient, a substantial amount of lateral movement is allowed, which avoids discomforting pressure around the waist normally produced by conventional waist belts and the like.

The jacket is preferably made from a stong flexible material such as cotton fabric, although the jacket also can be made from nylon. The attendant waist straps and loops are preferably made from a strong flexible material such as nylon.

I claim:

1. A restraining device for comfortably holding a patient in a hospital bed or wheelchair, the restraining device comprising:

a jacket disposed around the upper torso of the patient so that it makes a snug fit around the shoulders of the patient and extends downwardly around the midriff of the patient, the jacket having sleeves for extending along the arms of the patient to provide means of restraint for the patient;

a pair of right side ties spaced apart circumferentially from one another on the right side of the midriff region of the jacket, and a pair of left side ties spaced apart circumferentially from one another on the left side of the midriff region of the jacker, each pair of spaced apart ties having inner ends securely affixed to the jacket midriff region and free ends spaced from the jacket so the ties on each side of the jacket can be fastened to one another for adjusting the circumferential size of the jacket midriff region to fit the size of the patient and for retaining the adjusted size of the jacket; and fastening means securely affixed to the front of the midriff region of the jacket and extending away from opposite sides of the jacket for attachment to a fixture located remotely from the jacket worn by the patient.

2. Apparatus according to claim 1 in which the rear of the jacket opens along a pair of marginal edges; and including means for securing the marginal edges of the jacket so that the secured marginal edges of the jacket are offset from the rear center of the jacket.

3. Apparatus according to claim 1 including restraining means on the rear shoulder regions of the jacket for use in attachment to the fixture.

4. Apparatus according to claim 1 including a restraining strap for extending from the front to the rear of the jacket; and front and rear restraining means attached to the front and rear of the jacket, respectively, for attachment to front and rear portions of the restraining strap so the attached restraining strap extends under the jacket from the front restraining means to the rear restraining means to prevent the patient from sliding down in the fixture.

5. Apparatus according to claim 1 in which the fastening means on the midriff region of the jacket comprises an elongated waist strap having a central region securely affixed to the midriff region of the jacket with opposite right and left flexible free end portions of the waist strap of greater length than the right and left side ties extending away from opposite sides of the jacket for attachment remotely to the fixture.

6. A restraining device for comfortably and securely holding a patient in a hospital bed or a wheelchair, the restraining device comprising:

a jacket disposed around the upper torso of the patient so that the jacket makes a snug fit around the shoulders of the patient and extends downwardly and continuously around the midriff of the patient, the jacket having sleeves for extending along the arms of the patient;

a pair of right side ties spaced apart circumferentially from one another on the right side of the midriff region of the jacket, and a pair of left side ties spaced apart circumferentially from one another on the left side of the midriff region of the jacket, each pair of spaced apart ties having inner ends securely affixed to the jacket midriff region and free ends spaced from the jacket so the ties on each side of the jacket can be fastened to one another for adjusting the circumferential size of the jacket midriff region to fit the size of the patient and for retaining the adjusted size of the jacket;

fastening means on the midriff region of the jacket comprising an elongated waist strap having a central region securely affixed only to the front of the midriff region of the jacket with opposite right and left flexible free end portions of the waist strap extending away from opposite sides of the jacket for attachment to a fixture located remotely from the jacket worn by the patient;

a flexible restraining strap for extending under the jacket from the front to the rear of the jacket; and front and rear restraining means affixed to the front and rear of the jacket midriff section, respectively, for attachment to front and rear portions of the restraining strap so the attached restraining strap extends under the jacket from the front restraining means to the rear restraining means to prevent the patient from sliding down in the fixture.

7. Apparatus according to claim 6 in which the rear of the jacket opens along a pair of marginal edges; and including means for securing the marginal edges of the jacket so that the secured marginal edges of the jacket are offset from the rear center of the jacket.

8. Apparatus according to claim 7 including shoulder restraining means on the rear shoulder regions of the jacket for use in attachment to the fixture.

* * * * *